(12) United States Patent
Velasco

(10) Patent No.: US 8,813,627 B2
(45) Date of Patent: Aug. 26, 2014

(54) METHOD AND SYSTEM TO DETECT IMPROVISED EXPLOSIVE DEVICES

(76) Inventor: Francisco Velasco, Sanford, FL (US)

( * ) Notice: Subject to any disclaimer, the term of this patent is extended or adjusted under 35 U.S.C. 154(b) by 24 days.

(21) Appl. No.: 13/470,834

(22) Filed: May 14, 2012

(65) Prior Publication Data

US 2013/0301032 A1 Nov. 14, 2013

(51) Int. Cl.
*G01N 21/33* (2006.01)
*G01N 21/64* (2006.01)
*B05D 5/00* (2006.01)
*C09K 11/00* (2006.01)

(52) U.S. Cl.
USPC ... 89/1.11; 89/1.1; 86/50; 356/51; 252/408.1; 427/136

(58) Field of Classification Search
USPC ........... 89/1.1, 1.11, 1.13, 1.2; 86/50; 356/51; 252/408.1; 427/136
See application file for complete search history.

(56) References Cited

U.S. PATENT DOCUMENTS

| | | | | |
|---|---|---|---|---|
| 2,905,572 | A * | 9/1959 | Jones | 428/426 |
| 2,952,192 | A * | 9/1960 | Nagin | 404/72 |
| 3,414,368 | A * | 12/1968 | Minemura et al. | 8/456 |
| 3,901,793 | A * | 8/1975 | Buchot et al. | 209/3.3 |
| 3,973,466 | A * | 8/1976 | Marcus et al. | 89/1.11 |
| 4,481,422 | A * | 11/1984 | deMarco et al. | 250/459.1 |
| 5,734,167 | A * | 3/1998 | Skelly | 250/458.1 |
| 5,942,483 | A * | 8/1999 | Leu | 510/326 |
| 6,533,961 | B2 * | 3/2003 | Harelstad et al. | 252/301.35 |
| 6,592,048 | B2 * | 7/2003 | Motoki et al. | 239/8 |
| 6,713,624 | B1 * | 3/2004 | Doane et al. | 536/45 |
| 8,253,115 | B1 * | 8/2012 | Stevens et al. | 250/458.1 |
| 2002/0002929 | A1 * | 1/2002 | Harelstad et al. | 106/31.04 |
| 2002/0045010 | A1 * | 4/2002 | Rohrbaugh et al. | 427/372.2 |
| 2002/0131046 | A1 * | 9/2002 | Christy et al. | 356/445 |
| 2003/0102460 | A1 * | 6/2003 | Harelstad et al. | 252/301.35 |
| 2005/0150371 | A1 * | 7/2005 | Rickard | 89/1.11 |
| 2006/0263536 | A1 * | 11/2006 | Blair et al. | 427/421.1 |
| 2007/0209647 | A1 * | 9/2007 | MacCarty | 124/56 |
| 2011/0081723 | A1 * | 4/2011 | Miller et al. | 436/56 |
| 2011/0293968 | A1 * | 12/2011 | Leung et al. | 429/7 |
| 2012/0064134 | A1 * | 3/2012 | Bourke et al. | 424/401 |
| 2013/0047701 | A1 * | 2/2013 | Peltz et al. | 73/23.2 |
| 2013/0110455 | A1 * | 5/2013 | Scholes et al. | 702/150 |

* cited by examiner

*Primary Examiner* — Bret Hayes
(74) *Attorney, Agent, or Firm* — McKinney Law, PLLC

(57) ABSTRACT

A method and system to detect an improvised explosive device is disclosed. In a particular embodiment, the method includes dispersing a mixture containing a fluorescent material uniformly over a ground cover, illuminating the ground cover with wavelengths of visible light or ultraviolet (UV) light causing the fluorescent material to fluoresce in a visible light spectrum, and detecting where the mixture has been disturbed on the ground cover by visually observing inconsistencies in the fluorescent material on the ground cover that is fluorescing to indicate a location of the improvised explosive device. The method also includes that the mixture is adapted to cling to a person, clothes, or any combination thereof, upon contact.

12 Claims, 2 Drawing Sheets

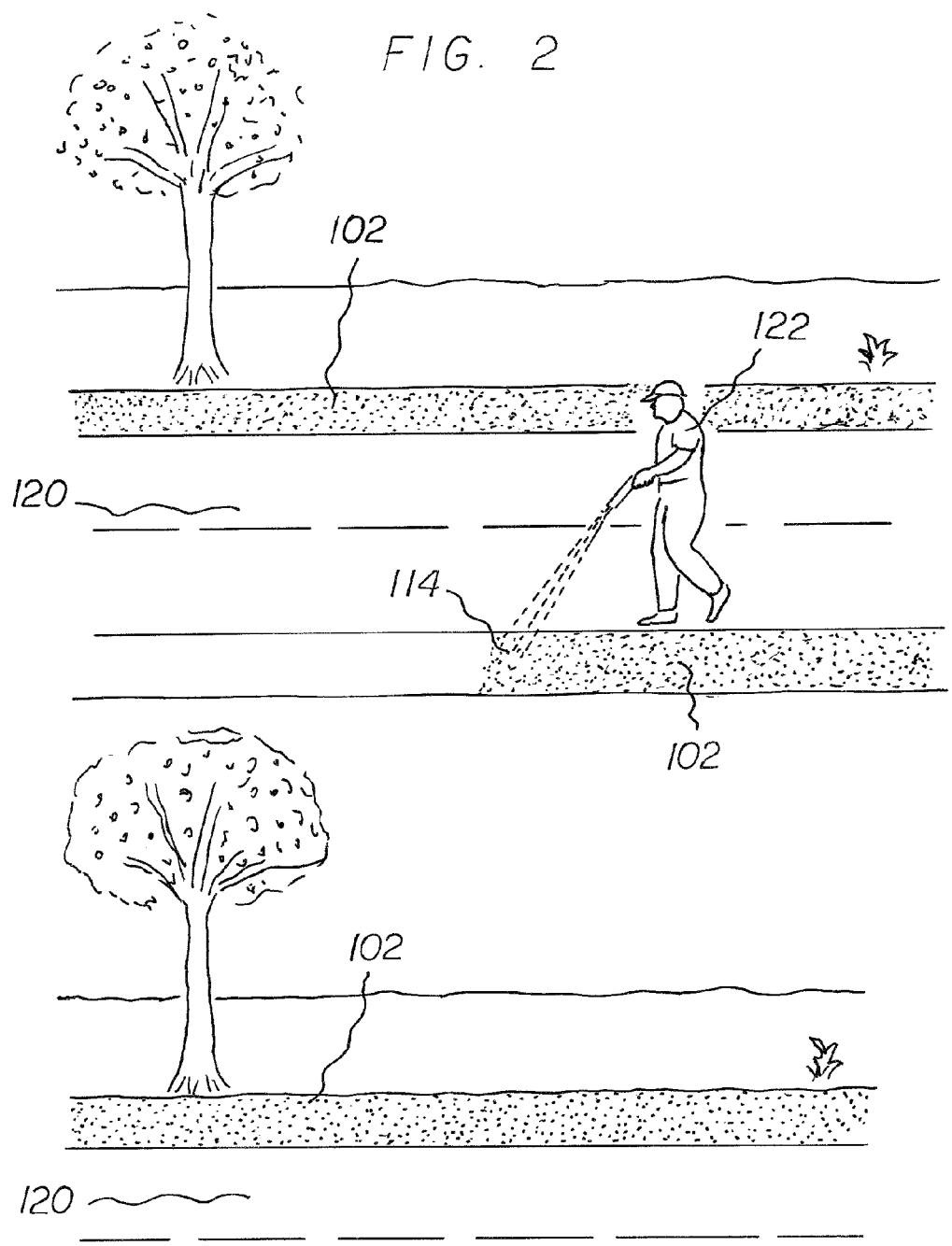

METHOD AND SYSTEM TO DETECT IMPROVISED EXPLOSIVE DEVICES

I. FIELD

Figure 1:
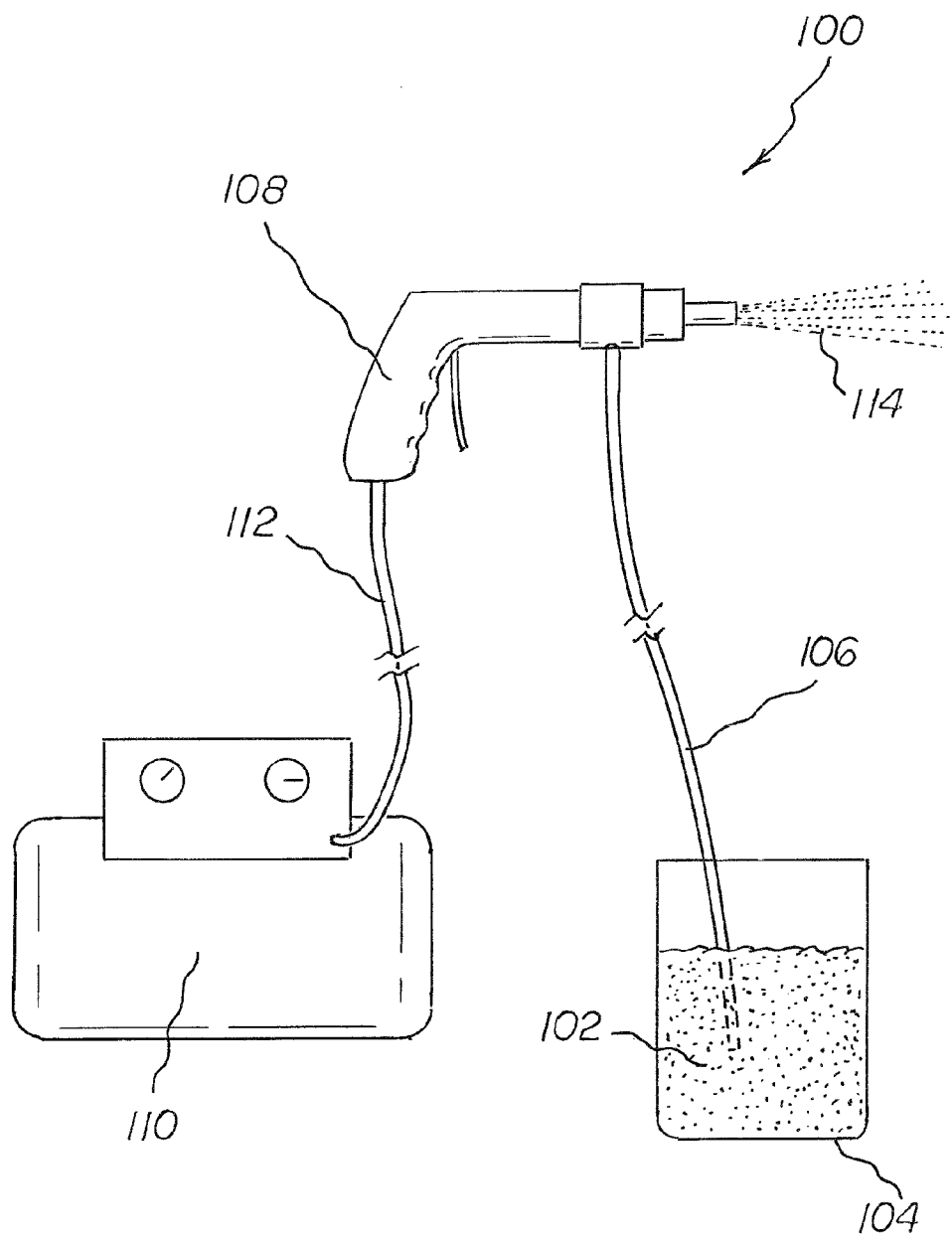

The present invention relates in general to the field of security systems, and in particular to a method and system to detect improvised explosive devices.

II. DESCRIPTION OF RELATED ART

Present conflicts abroad have increased the development of asymmetrical tactics utilized by terrorists to inflict injury and death. Specifically, the multi-faucet combat deterrent well known as the improvised explosive device (IED) has been a key resource utilized by terrorist. As technology has been continually refined to address the inhibiting and locating of IEDs, the development of unconventional tactics by terrorists have evolved linearly countering conventional science and military strategy. In particular, when IEDs have been successfully located, the identities of the individuals who placed the IEDs are unknown. Therefore, unless an eyewitness is able to identify a particular individuals or the individuals voluntarily admit to placing the IED through interrogation techniques, the individuals will continue their harmful and injurious methods of operation.

Therefore, a need exists in the art for a method and system to detect IEDs that is effective in not only detecting the location of IEDs, but also effective in being able to identify particular individuals responsible for placement of the IEDs.

However, in view of the prior art at the time the present invention was made, it was not obvious to those of ordinary skill in the pertinent art how the identified needs could be fulfilled.

III. SUMMARY

In a particular embodiment, a method of detecting improvised explosive devices is disclosed. The method includes preparing a mixture of ingredients adapted to camouflage with a desired ground cover, and adding a fluorescent material to the mixture. The ingredients may include sand, soil, organic material, or any combination thereof. The ingredients may also include sodium carbonate and sodium silicate. The method also includes adding an adhesive to the mixture, where the adhesive is adapted to cause the mixture to cling to a person, clothes, or any combination thereof, upon contact. A coagulant may be added to the mixture to help bind the mixture together. The coagulant may be wheat flour, for example. In addition, the method includes spraying the mixture with a liquid to moisten the mixture, compacting the mixture, and drying the mixture. The dried mixture may then fragmentized into pieces of a desired size. The mixture containing the fluorescent material may be uniformly disbursed over a ground cover. The method includes illuminating the ground cover with wavelengths of visible light or ultraviolet (UV-A) light, e.g., "black light", causing the fluorescent material to fluoresce in a visible light spectrum. Further, the method includes detecting where the mixture has been disturbed on the ground cover by visually observing inconsistencies in the fluorescent material on the ground cover that is fluorescing to indicate a location of the improvised explosive device.

In another particular embodiment, a system to detect an improvised explosive device is disclosed. The system includes a mixture having a fluorescent material to uniformly disperse over a ground area, where the mixture is adapted to camouflage with the ground cover, and an illumination source to illuminate the ground cover with wavelengths of visible light or ultraviolet (UV-A) light causing the fluorescent material to fluoresce in a visible light spectrum. The mixture may be a granular material. The system may also include a pneumatic sprayer to disperse the mixture over the ground area.

In another particular embodiment, a method to detect to an improvised explosive device is disclosed. The method includes dispersing a mixture containing a fluorescent material uniformly over a ground cover, illuminating the ground cover with wavelengths of visible light or ultraviolet (UV-A) light causing the fluorescent material to fluoresce in a visible light spectrum, and detecting where the mixture has been disturbed on the ground cover by visually observing inconsistencies in the fluorescent material on the ground cover that is fluorescing to indicate a location of the improvised explosive device. The ground cover may be along side a roadway, for example. In addition, a pneumatic sandblaster may be used for dispersing the mixture or the mixture may be disbursed by hand. The mixture is adapted to cling to a person, clothes, or any combination thereof, upon contact.

Other aspects, advantages, and features of the present disclosure will become apparent after review of the entire application, including the following sections: Brief Description of the Drawings, Detailed Description, and the Claims.

IV. BRIEF DESCRIPTION OF THE DRAWINGS

FIG. 1 is a particular embodiment of a system to detect an improvised explosive device (IED);

FIG. 2 is a particular embodiment of a method to detect an improvised explosive device by uniformly applying a camouflaged fluorescent mixture along side a road that has previously been cleared of IEDs; and FIG. 3 depicts that subsequently illuminating the mixture with UV-A light shows an area that has been disturbed indicating that IED may have been placed in that location after the mixture was applied.

V. DETAILED DESCRIPTION

The method and system effectively identifies the positioning of roadside improvised explosive devices (IED) and hidden caches of ordnance and is particularly effective during nighttime operations. Chemical fluorescent materials are utilized and integrated with tactical dispersion methods to enhance the detection of IEDs. The special optical deterrent (SOD) mixture is sand like camouflaged material that may be sprayed evenly along the side of the roads in areas of potential IED placement sites during route reconnaissance. When following missions are conducting the same or similar paths during the evenings, the use of UV-A light will detect dig cites for IEDs as the fluorescent material of the mixture will begin to fluoresce in a visible light spectrum under the UV-A light. The mixture may also be placed in rural areas where caches of ordnance are expected to be concealed leading to their excavation. Secondary use of this mixture can aid in force protection for facilities that may be infiltrated by combatants. Specifically, dispensing the mixture around the perimeter will allow for intrusion detection. The method and system is also effective in identifying clandestine airstrips, paths, tunnels, and international borders, for example. The mixture will allow military forces and government forces to discriminate between legitimate and illegitimate activity, ultimately serving as a deterrence/denial system to insurgents and criminal elements utilizing covert.

Referring now to FIG. 1, the system 100 may include the fluorescent mixture 102 contained in a reservoir 104. One end of a hose 106 is placed in the mixture 102 and a second end of the hose 106 is connected to a sandblaster gun 108 via compressor hose 112. Accordingly, when a trigger of the sandblaster gun 108 is pulled, the mixture 102 is pulled from the reservoir 104 up the hose 106 and into the gun 108 that is fired out of the barrel as a spray 114. The dispersion of the mixture may be done with the sandblaster described above or similar type tools or by hand. The air compressor 110 may be gasoline or electric. For example, an inverter may be connected to a battery of a vehicle to an electric compressor 110 that is utilized to help disburse the mixture 102. The system 100, or any components thereof, may be mounted any where on the vehicle such as a front bumper, or rolled off the vehicle as long as a power source is provided.

As shown in FIG. 2, the sand like mixture 102 is sprayed 114 over the areas of interest along side a road 120 by an operator 122. The mixture 102 is at least partially adhesive and is adapted to cling to a person, clothes, or any combination thereof, upon contact. For example, after spraying the mixture over a desired ground cover of areas suspected of IEDs, an even color is depicted across the surface when the mixture is illuminated by UV-A light. In FIG. 2, the mixture 102 is illustrated as to how it would look when illuminated by UV-A light. Otherwise, without being illuminated by UV-A light, the mixture 102 is virtually invisible to the naked eye under natural light conditions and light from a flashlight, for example.

When the individual or individuals cross an area that has been sprayed with the mixture 102, and place the IED, the individual(s) involved intrude on the area sprayed and cause a color discrepancy 130 in the mixture 102 that is visible under UV-A light as shown in FIG. 3. This color discrepancy 130 allows for the individuals identifying the IED to follow the disturbed path (i.e., color discrepancy 130) to the IED placement site. Further, when the individual or individuals dig and place the IED(s), they physically touch the mixture 102 with both hands and clothing. The mixture 102 unnoticeable sticks to the clothing and individual, which later can be identified when these individual(s) leave the IED placement site by focusing the UV-A light on the suspected individuals and their clothes. The UV-A light causes the fluorescent material in the mixture 102 to illuminate verifying which individuals had contact with the mixture 102, and thus were involved with placing the IED.

In an effort to locate covert airstrips, paths and tunnels, the mixture 102 may be sprayed over the ground cover in the areas of interest so than those areas will appear different than that of the surrounding sand and terrain under a UV-A light. When a plane lands on this covert strip covered with the mixture 102, the activity of the plane landing causes a color discrepancy when illuminated with the UV-A light. The length of the "lines" visible in the area covered with the mixture 102 along with the spacing will indicate aircraft use.

Also, the method and system may be used to enhance force protection by spraying the mixture 102 around the perimeter of an area of the facility to be secured, for example. When infiltration of the secured facility occurs on the ground, the individuals involved will disrupt the mixture 102 causing a color discrepancy that is visible under the UV-A light indicating the path and area infiltrated.

As another example, the method and system enhances the discovery of caches in ordnance by spraying the ground cover in the suspected areas of hidden caches with the mixture 102. When individual(s) hide ordnance or recover ordnance from the caches in the area sprayed, they will cross the mixture 102 causing a disruption in color. This disruption in color that is visible under UV-A light will indicate the path traveled and the area that has been dug up.

The mixture 102 may be used as borders by detecting the early stages of movement and intrusions in remote areas used by criminal organizations. By spraying the mixture 102 along the areas identified as the international boundary, for example, the individuals who cross this area will cause a disruption in color visible under UV-A light. This disruption will indicate the area crossed.

The mixture 102 may be prepared in the field using commonly found items such as laundry detergent, a plastic sheet, water, and wheat flour, for example. An approximately ¼ inch layer of the laundry detergent containing sodium carbonate, sodium silicate, surfactants, soil suspending agent, and optical brighteners (i.e., fluorescent material), is spread out over the plastic sheet. The mix is lightly sprayed with warm water and covered with an approximately ⅛ inch layer of the wheat flour. The plastic is rolled into a snug cigar shape and left for approximately 12 hours at room temperature. After approximately 12 hours, the mixture may be separated and broken into finer sand like material that is congruent with the ground cover and terrain it will be used in.

The operator 122 may wear a respirator along with gloves and eye protection. In operation, the reservoir 104 is filled with the fluorescent mixture 102. A thin layer of mixture 102 is sprayed using the sandblaster 108 beginning approximately 12 inches from the road 120 to an additional 48 inches outward and is adjusted according to the ground cover, terrain and past TED placement distance from the road. When spraying, the nozzle elevation from the ground may be adjusted to a level that allows for an even dispersal of mixture 102 with minimal dust. The operator 122 avoids stepping on the area covered by mixture post-spraying as this may cause a disruption in color visible under UV light.

When the mixture 120 is hand applied, the operator 122 may wear a respirator along with gloves and eye protection. The operator 122 fills a cup or gallon bucket with the mixture 102. The operator 122 spreads a thin layer of the mixture beginning 12 inches from the road 120 to an additional 48 inches outward and adjusts according to terrain and past TED placement distance from the road by hand in a sweeping motion. When spreading the mixture 102 by hand, the operator 122 ensures that dispersal is done at an elevation from the ground that allows for an even dispersal of mixture 102 with minimal dust. The operator 122 also avoids stepping on the area covered by mixture post-spraying as this may cause a disruption in color visible under UV-A light.

Utilizing the UV-A light fixtures, the beams are focused to the areas applied with the fluorescent mixture 102. The mixture 102 will appear purple, blue or a combination of purple-blue. When this appearance is disrupted there will be a break in color (black). This indicates possible IED placement and allows for a quick examination of the focal point. When encountering a daisy chain of IEDs, a similar displacement of color is consecutively visible. For areas with command detonated IEDs, the mixture 102 is sprayed outward from the road 120 as far as possible. This will detect not only the placement area of the IEDs, but will trace the wire(s) used for command detonation back to the location of the combatant. In general, detection of the IEDs is completed at night so that the fluorescent is more visible, but can also be used in daylight although the contrast may be less than when used at nighttime. The mixture 102 may also be applied to rural areas where caches are expected to be hidden. A similar procedure is followed by looking for a color disruption in the fluorescent material that is visible under the UV-A light.

The previous description of the disclosed embodiments is provided to enable any person skilled in the art to make or use the disclosed embodiments. Various modifications to these embodiments will be readily apparent to those skilled in the art, and the principles defined herein may be applied to other embodiments without departing from the scope of the disclosure. Thus, the present disclosure is not intended to be limited to the embodiments shown herein but is to be accorded the widest scope possible consistent with the principles and novel features as defined by the following claims.

What is claimed is:

1. A method to detect an improvised explosive device, the method comprising:
   preparing a mixture of ingredients adapted to camouflage with a desired ground cover;
   adding a fluorescent material to the mixture;
   adding a coagulant to the mixture, wherein the coagulant is wheat flour;
   adding an adhesive to the mixture, wherein the adhesive is adapted to cause the mixture to cling to a person, clothes, or any combination thereof, upon contact;
   spraying the mixture with a liquid to moisten the mixture; and
   compacting the mixture.

2. The method of claim 1, further comprising drying the mixture.

3. The method of claim 2, further comprising fragmentizing the mixture into pieces of a desired size.

4. The method of claim 3, further comprising dispersing the mixture containing the fluorescent material uniformly over a ground cover.

5. The method of claim 4, further comprising illuminating the ground cover with wavelengths of visible light or ultraviolet (UV) light causing the fluorescent material to fluoresce in a visible light spectrum.

6. The method of claim 5, further comprising detecting where the mixture has been disturbed on the ground cover by visually observing inconsistencies in the fluorescent material on the ground cover that is fluorescing to indicate a location of the improvised explosive device.

7. A method to detect an improvised explosive device, the method comprising:
   dispersing a mixture uniformly over a ground cover, wherein the mixture contains a wheat flour coagulant and a fluorescent material;
   illuminating the ground cover with wavelengths of visible light or ultraviolet (UV) light causing the fluorescent material to fluoresce in a visible light spectrum; and
   detecting where the mixture has been disturbed on the ground cover by visually observing inconsistencies in the fluorescent material on the ground cover that is fluorescing to indicate a location of the improvised explosive device.

8. The method of claim 7, wherein the ground cover is along side a roadway.

9. The method of claim 7, further comprising using a pneumatic sandblaster for dispersing the mixture.

10. The method of claim 7, wherein the mixture is adapted to cling to a person, clothes, or any combination thereof, upon contact.

11. The method of claim 7, further comprising dispersing the mixture on the ground cover by hand.

12. A system to detect an improvised explosive device, the system comprising:
   a mixture having a wheat flour coagulant and fluorescent material to uniformly disperse over a ground area, wherein the mixture is adapted to camouflage with the ground cover and the fluorescent material of the mixture will fluoresce in a visible light spectrum when the ground cover is illuminated with wavelengths of visible light or ultraviolet (UV) light; and
   a pneumatic sprayer to disperse the mixture over the ground area.

* * * * *